United States Patent [19]

Mazurik et al.

[11] Patent Number: 5,354,285
[45] Date of Patent: Oct. 11, 1994

[54] INJECTION SYRINGE

[75] Inventors: Sergej M. Mazurik, Lenina Str. 92/57, Poltava, Ukraine 314022; Andrej N. Sokolov; Marat M. Kashlykov, all of Poltava, Ukraine

[73] Assignee: Sergej Mikhailovich Masurik, Poltava, Ukraine

[21] Appl. No.: 113,354

[22] Filed: Aug. 30, 1993

Related U.S. Application Data

[63] Continuation of Ser. No. 851,391, Mar. 16, 1992, abandoned.

[30] Foreign Application Priority Data

Nov. 29, 1991 [SU] U.S.S.R. .................... 5015271

[51] Int. Cl.$^5$ ................................................ A61M 5/00
[52] U.S. Cl. ...................................... 604/191; 604/207; 604/218
[58] Field of Search ............... 604/191, 218, 187, 207, 604/208

[56] References Cited

U.S. PATENT DOCUMENTS

| | | | |
|---|---|---|---|
| 778,879 | 1/1905 | Molinari | 604/218 X |
| 2,515,956 | 7/1950 | Greenberg | 604/207 |
| 3,477,492 | 11/1969 | Shaw | |
| 3,749,084 | 7/1973 | Cucchiara | 604/191 |
| 3,838,689 | 10/1974 | Cohen | |
| 4,188,949 | 2/1980 | Antoshkiw | 604/191 |
| 4,583,978 | 4/1986 | Porat et al. | |
| 4,702,737 | 10/1987 | Pizzino | |
| 4,915,695 | 4/1990 | Koobs | 604/191 |

FOREIGN PATENT DOCUMENTS

| | | |
|---|---|---|
| 0115931 | 8/1984 | European Pat. Off. |
| 0167662 | 1/1986 | European Pat. Off. |
| 0363338 | 4/1990 | European Pat. Off. |
| WO84/00011 | 1/1984 | PCT Int'l Appl. |

Primary Examiner—John D. Yasko
Attorney, Agent, or Firm—Spencer, Frank & Schneider

[57] ABSTRACT

The injection syringe which is particularly used for medical purposes. The syringe has a body, a piston which is disposed in the syringe body for displacement therein and an injection needle. The piston has at least two piston elements, 3 which are displaceable in relation to each other along the longitudinal axis of the syringe body.

6 Claims, 6 Drawing Sheets

INJECTION SYRINGE

This application is a continuation of application Ser. No. 07/851,391, filed Mar. 16, 1992 now abandoned.

BACKGROUND OF THE INVENTION

The invention relates to an injection syringe which is particularly used for medical purposes, the injection syringe including a syringe body, a piston being disposed in the syringe body for displacement therein, and an injection needle being located at the front end of the syringe body.

What is known is an ordinary injection syringe usually used for intravascular injections (for example, a product of the firm "Becton Dickinson" having a volume of 20 ml) and having a cylindrical syringe body, a piston with a piston rod and an injection needle. In most cases a mixture of medical substances is injected with this injection syringe, the mixture containing a minor amount of an active ingredient and a large amount of a diluent.

A disadvantage of this injection syringe is that it is not possible to precisely draw up a low dose of an active ingredient (for example 0.3-0.5 ml) due to the large volume of the injection syringe.

What is also known is an ordinary injection syringe (for example, a product of the firm "Becton Dickinson" having a volume of 1 ml) which also has a cylindrical body, a piston and a piston rod and a injection needle, and which enables a user to draw up a very precise amount of an active ingredient. However, intravascular injections cannot be carried out with this injection syringe, as for most intravascular injections it is necessary to draw up 0.3-0.5 ml of an active ingredient and to mix it with 10-20 ml of a diluent.

The problem underlying the invention is to provide an injection syringe by simple construction with which precise doses of an active ingredient and of a diluent can be drawn up.

SUMMARY OF THE INVENTION

Starting out from the injection syringe of the generic kind, this problem is solved by a piston including at least two piston elements which can be displaced in relation to each other along the longitudinal axis of the syringe body.

One rod is mounted on the side of each piston element which is remote from the injection needle so that the corresponding piston element can be pulled out or pushed in, respectively.

In order to be able to read the precise amount of a dose two scales having different gradations can be provided, the more precise scale being used for reading the amount of an active ingredient and the less precise for reading the amount of diluent.

In one embodiment of the invention the piston rod of one piston element has a central channel, the inner diameter thereof corresponding to the outer diameter of the other piston element arranged in the central channel, the less precise scale being provided on the syringe body and the more precise scale being provided on one of the piston rods.

In another embodiment of the invention both piston elements are arranged in the syringe body in such a manner that their outer surfaces are in contact with the inner surface thereof, both piston elements forming a cylinder, when they are disposed adjacent to each other, the outer diameter of the cylinder corresponding to the inner diameter of the syringe body. The scales of different gradation are provided on the cylindrical syringe body.

The injection syringe according to the invention has a high dosing accuracy when drawing up and diluting a substance. It can be easily produced and is reliable. The costs for producing the injection syringe according to the invention hardly exceed the costs for producing the syringes which are presently known.

BRIEF DESCRIPTION OF THE DRAWINGS

In the following, embodiments of the invention are further explained by means of the accompanying drawings, wherein.

DETAILED DESCRIPTION OF THE PREFERRED EMBODIMENTS

Figure 1:
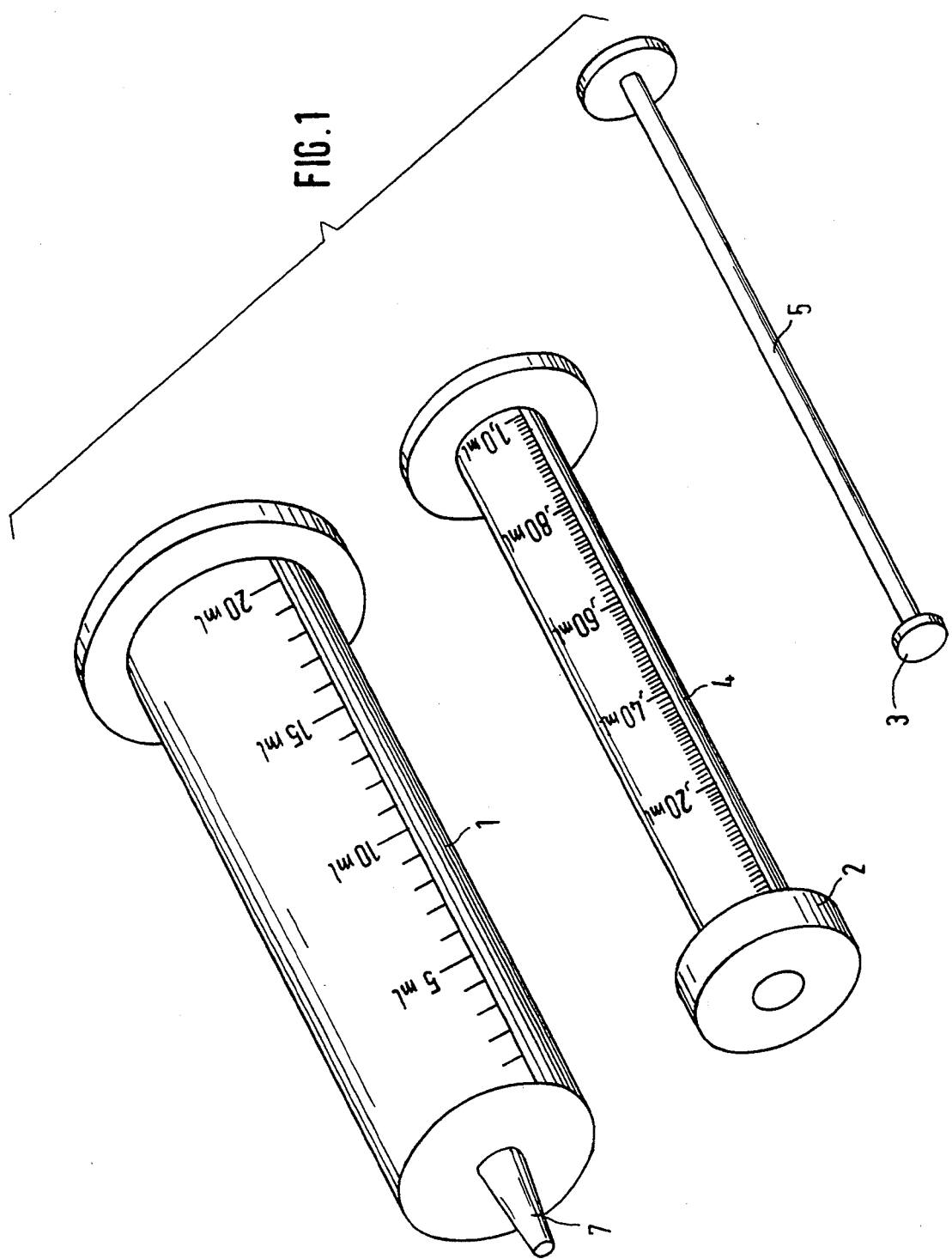
FIG. 1 shows a first embodiment of an injection syringe in disassembled form.

The injection syringe shown in FIGS. 1, 3, 5 and 6 includes a cylindrical or tubular syringe body 1 and a cylindrical piston 10 which is arranged in the syringe body 1 in such a manner that it can be displaced therein. A conical holding device 7 for an injection needle 6 is located at the front end of the syringe body 1. The injection needle 6 can either be detachable or fixed.

The piston 10 consists of two piston elements 2 and 3 which can be displaced in relation to each other along the longitudinal axis of the syringe body 1. The outer diameter of the first piston element 2 corresponds to the inner diameter of the syringe body 1. A piston rod 4 is mounted on the side of the first piston element 2 which is remote from the injection needle 6. A central channel 8, in alignment with the longitudinal axis of the syringe body 1 and having a constant diameter, runs through the piston rod 4 and the first piston element 2. The second cylindrical piston element 3 is arranged in this central channel 8 in such a manner that it can be displaced. The outer diameter of the second piston element 3 corresponds to the inner diameter of the central channel 8. A piston rod 5 is also mounted on the side of the second piston element 3 which is remote from the injection needle 6.

On the syringe body 1 there is a coarse scale (FIG. 1) having a gradation of 1 ml for example. The piston rod 5 of the second piston element 3 is marked with a fine scale having a gradation of 0.05 ml for example (FIG. 1).

Figure 5:
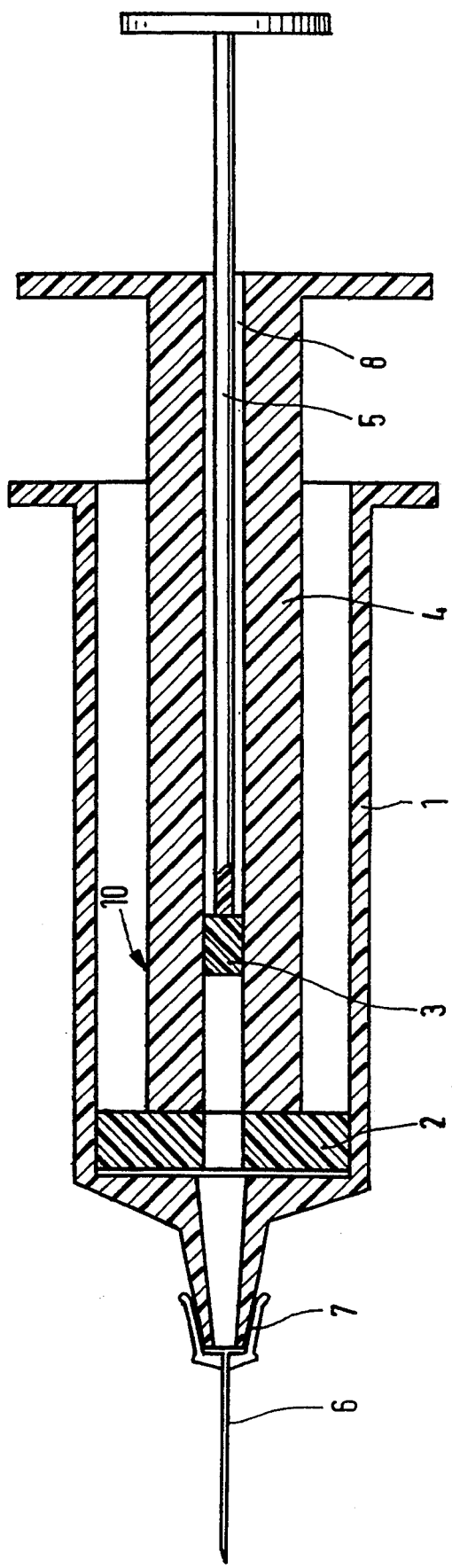
FIG. 5 shows a longitudinal cross-section of the injection syringe of FIG. 1 at the moment of drawing up a small dose of an active ingredient.

If an injectable solution is drawn up with this injection syringe, the end of the injection needle 6 is immersed into an ampoule or vial containing an active ingredient, and the second piston element 3 is slightly pulled out of the central channel 8 of the piston rod 4 of the first piston element 2. Thus, a vacuum is created in the central channel 8 and the active ingredient flows from the ampoule through the injection needle 6 into the central channel 8 (FIG. 5). This guarantees that the active ingredient can be drawn up with a precision of 0.05 ml since the piston rod 5 has such a gradation. If more than one milliliter of the strong active ingredient, for example 1.25 ml, are to be drawn up, this scale and the scale on the body 1 will be used together.

Figure 6:
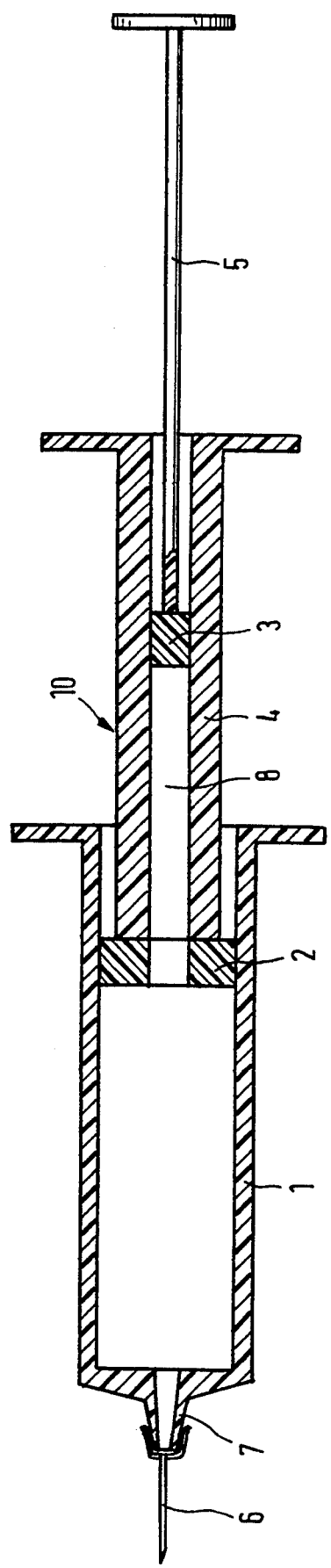
FIG. 6 shows a longitudinal cross-section of the injection syringe of FIG. 1 at the moment of drawing up a diluent.

After the active ingredient has been drawn up, the injection needle 6 is immersed into a diluent, and the first piston element 2 is displaced by pulling the corresponding piston rod 4 in a direction opposite to the injection needle 6. Thus, the necessary amount of diluent can be drawn up (FIG. 6).

Figure 2:
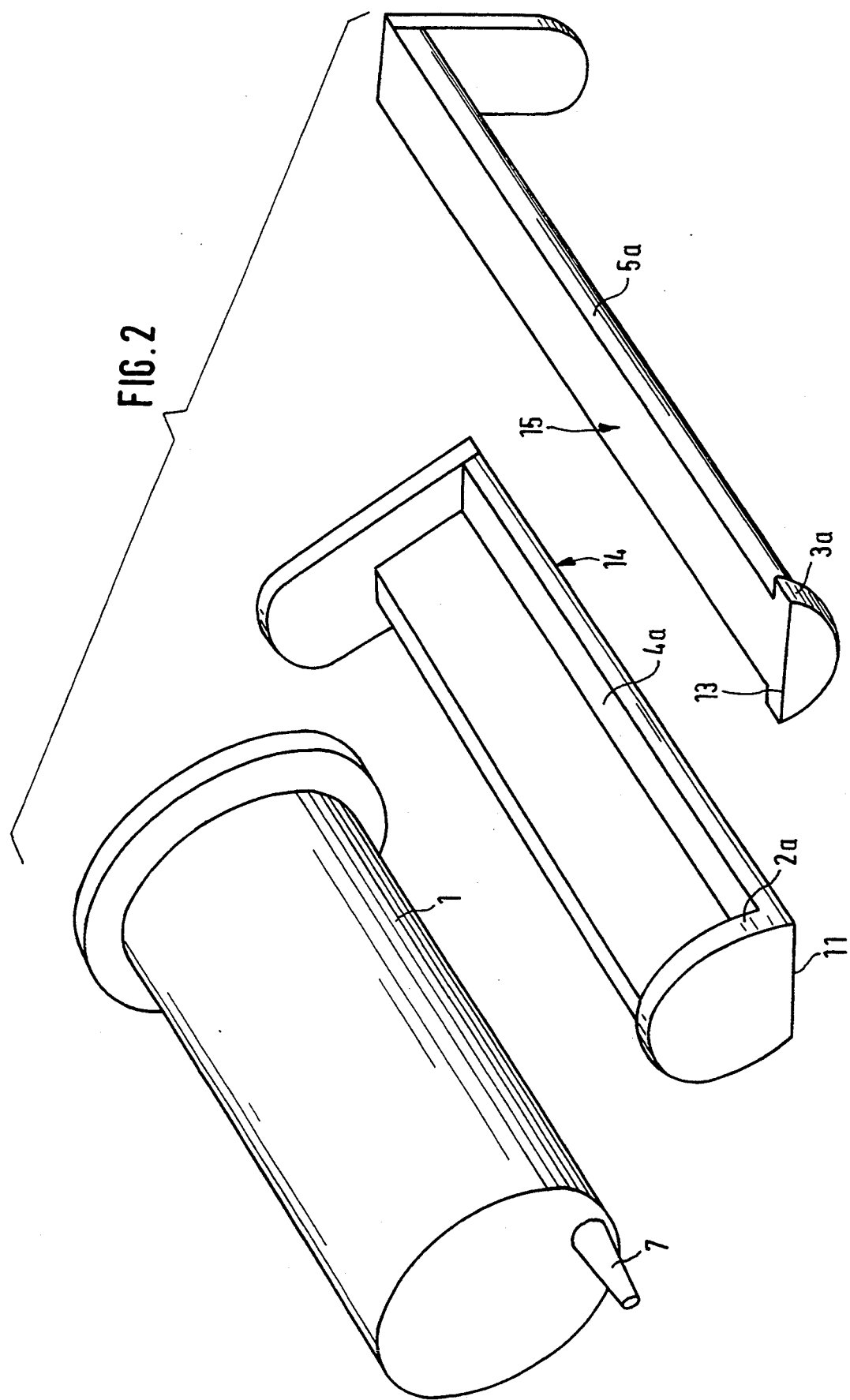
FIG. 2 shows a second embodiment of an injection disassembled form.
Figure 3:
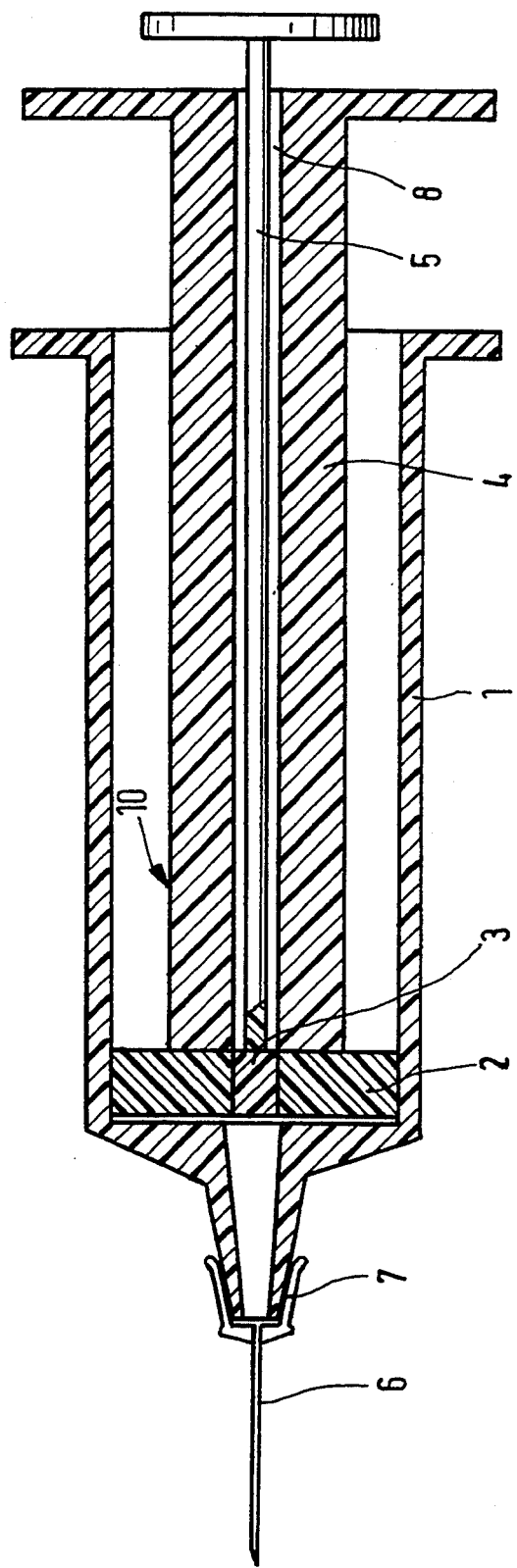
FIG. 3 shows a longitudinal cross-section of the injection syringe of FIG. 1.
Figure 4:
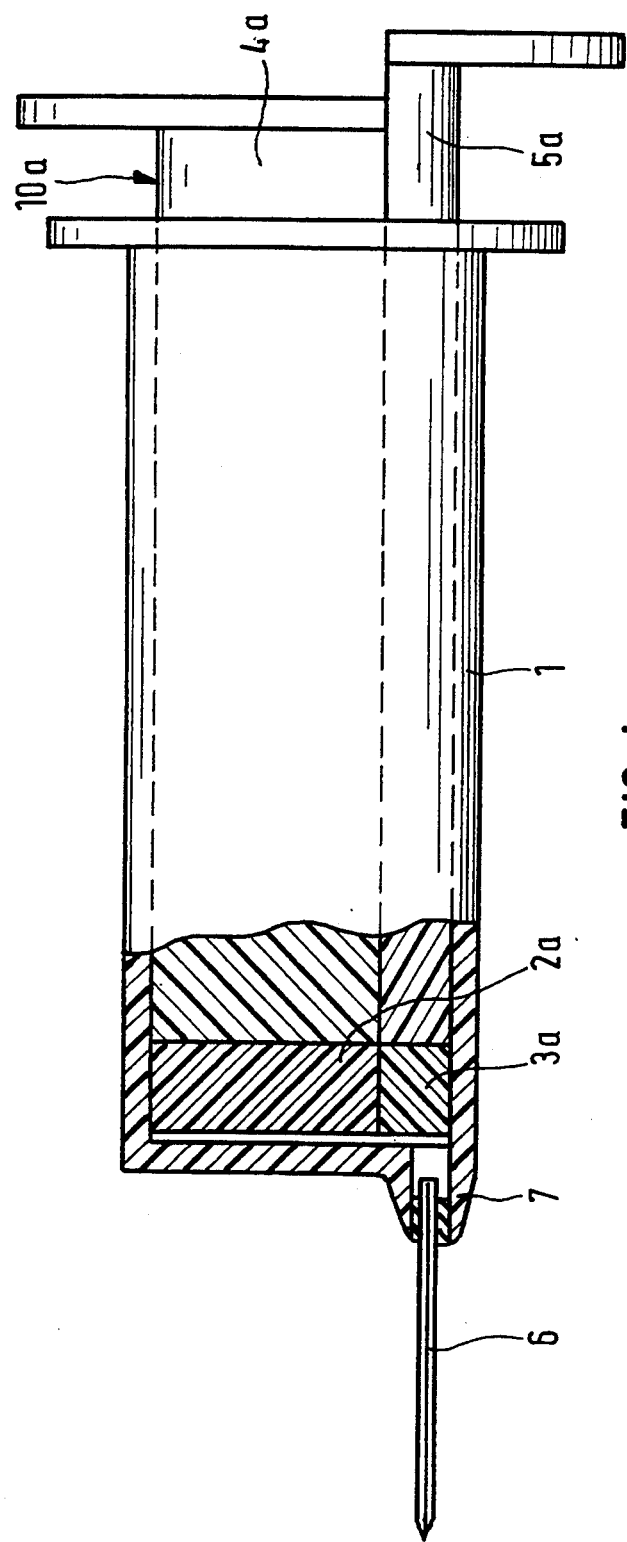
FIG. 4 shows a longitudinal cross-section of the injection syringe of FIG. 2.

In the embodiment of the injection syringe shown in FIGS. 2 and 4 the conical holding device 7 for the injection needle 6 is located at the area of edge of the front end of the syringe body 1. The piston consists of two adjacent piston elements 2a and 3a both of which have the form of a cylindrical segment. The front part thereof, which in general is circular, is limited by a straight chord 11 and 13, respectively. When both piston elements 2a and 3a and their straight chord 11, 13 are adjacent to each other they form a complete cylinder, with the outer diameter thereof corresponding to the inner diameter of the syringe body 1. Thus, the outer surfaces of both piston elements 2a, 3a are in contact with the inner surface of the syringe body 1. The cylindrical syringe body 1 is marked with scales of different gradation (not shown).

A piston rod 4a and 5a, respectively, is arranged at the side of each of the piston elements 2a, 3a which is remote from the injection needle 6. Each of the piston rods 4a and 5a have a surface 14 and 15, respectively lying in extension of the corresponding chord, the surface being parallel to the longitudinal axis of the syringe body 1. By these surfaces 14, 15 it is possible that both piston elements 2a and 3a can be disposed in relation to each other along the longitudinal axis of the syringe body 1.

The piston element 3a, the front surface of which is considerably smaller than the front surface of the first piston element 2a, is located directly before the conical holding device 7.

An injection solution is drawn up with the injection syringe shown in FIGS. 2 and 4 in the same manner as with the injection syringe shown in FIG. 1.

What is claimed is:

1. A syringe comprising:
a tubular body having a first longitudinal axis, a first inner diameter and a first gradation on a side of the tubular body;
a first cylindrical piston disposed within the tubular body and having a first end, a second end and a central channel passing through the first cylindrical piston from the first end to the second end, the central channel having a second inner diameter, the first cylindrical piston having a second longitudinal axis substantially aligned with the first longitudinal axis and a second gradation on a side of the first cylindrical piston;
a first piston element coupled to the first end of the first cylindrical piston and having a first outer diameter corresponding to the first inner diameter of the tubular body, wherein the first cylindrical piston and the first piston element are displaceable within the tubular body in a direction along the first longitudinal axis with displacement indicated by a position of the first piston element with respect to the first gradation on the side of the tubular body;
a second cylindrical piston disposed within the central channel of the first cylindrical piston and having a first end, a second end, and a third longitudinal axis substantially aligned with the first longitudinal axis; and
a second piston element coupled to the first end of the second cylindrical piston and having a second outer diameter corresponding to the second inner diameter of the central channel, wherein the second cylindrical piston and second piston element are displaceable within the central channel in a direction along the first longitudinal axis with displacement indicated by a position of the second piston element with respect to the second gradation on the side of the first cylindrical piston.

2. A syringe according to claim 1, wherein the second gradation is finer than the first gradation.

3. A syringe according to claim 1, wherein the first gradation indicates displacement of the first cylindrical piston and the first piston element in 1 milliliter increments, and the second gradation indicates displacement of the second cylindrical piston and the second piston element in at least 0.05 milliliter increments.

4. A syringe comprising:
a tubular body having a first end, a second end, a first longitudinal axis and a first inner diameter;
a first cylindrical piston disposed within the tubular body and having a first end, a second end and a central channel passing through the first cylindrical piston from the first end to the second end, the central channel having a second inner diameter, the first cylindrical piston having a second longitudinal axis substantially aligned with the first longitudinal axis;
a first piston element coupled to the first end of the first cylindrical piston and having a first outer diameter corresponding to the first inner diameter of the tubular body, wherein the first cylindrical piston and the first piston element are displaceable within the tubular body in a direction along the first longitudinal axis for changing a first volume within the tubular body defined by the first end and the inner diameter of the tubular body and a relative position of the first piston element with respect to the first end of the tubular body;
a second cylindrical piston disposed within the central channel of the first cylindrical piston and having a first end, a second end, and a third longitudinal axis substantially aligned with the first longitudinal axis;
a second piston element coupled to the first end of the second cylindrical piston and having a second outer diameter corresponding to the second inner diameter of the central channel, wherein the second cylindrical piston and second piston element are displaceable within the central channel in a direction along the first longitudinal axis for changing a second volume within the central channel defined by the first end and the inner diameter of the first cylindrical piston and a relative position of the second piston element with respect to the first end of the first cylindrical piston;
first gradation means formed on the side of the tubular body for indicating a change in the first volume; and second gradation means formed on the side of the first cylindrical piston for indicating a change in the second volume.

5. A syringe according to claim 4, wherein the second gradation means indicates finer changes in volume than the first gradation means.

6. A syringe according to claim 4, wherein the first gradation means indicates changes in volume in 1 milliliter increments, and the second gradation means indicates changes in volume in at least 0.05 milliliter increments.

* * * * *